United States Patent
Kessler et al.

(10) Patent No.: US 11,125,736 B2
(45) Date of Patent: Sep. 21, 2021

(54) METHOD FOR ASCERTAINING TREATMENT PARAMETERS OF A TEXTILE BY MEANS OF STRUCTURAL INFORMATION

(71) Applicant: Henkel AG & Co. KGaA, Duesseldorf (DE)

(72) Inventors: Arnd Kessler, Monheim am Rhein (DE); Christian Nitsch, Duesseldorf (DE); Lars Zuechner, Langenfeld (DE); Georg Wawer, Vienna (AT); Alexander Mueller, Monheim (DE)

(73) Assignee: HENKEL IP & HOLDING GMBH, Duesseldorf (DE)

( * ) Notice: Subject to any disclaimer, the term of this patent is extended or adjusted under 35 U.S.C. 154(b) by 212 days.

(21) Appl. No.: 16/318,017

(22) PCT Filed: Jul. 11, 2017

(86) PCT No.: PCT/EP2017/067337
§ 371 (c)(1),
(2) Date: Jan. 15, 2019

(87) PCT Pub. No.: WO2018/011173
PCT Pub. Date: Jan. 18, 2018

(65) Prior Publication Data
US 2019/0302091 A1   Oct. 3, 2019

(30) Foreign Application Priority Data

Jul. 15, 2016   (DE) ..................... 10 2016 212 979.1
Jun. 12, 2017   (DE) ..................... 10 2017 209 865.1

(51) Int. Cl.
| G01N 33/36 | (2006.01) |
| H04N 13/204 | (2018.01) |
| G01N 29/04 | (2006.01) |
| G06K 9/62 | (2006.01) |

(Continued)

(52) U.S. Cl.
CPC .......... *G01N 33/367* (2013.01); *D06F 33/00* (2013.01); *D06F 34/18* (2020.02); *D06F 39/00* (2013.01);
(Continued)

(58) Field of Classification Search
CPC . G01N 33/367; D06F 34/18; D06F 33/00–76; D06F 34/00–34; G06T 2207/30124
See application file for complete search history.

(56) References Cited

U.S. PATENT DOCUMENTS

| 5,475,201 A | 12/1995 | Pike |
| 6,784,997 B2 | 8/2004 | Lorenz et al. |

(Continued)

FOREIGN PATENT DOCUMENTS

| CN | 204097748 U | 1/2015 |
| DE | 19547736 A1 | 6/1997 |
| DE | 102011087274 A1 | 5/2013 |
| DE | 102013210996 A1 | 12/2014 |
| JP | S59178306 A | 10/1984 |

OTHER PUBLICATIONS

EPO, International Search Report and Written Opinion issued in International Application No. PCT/EP2017/067337 dated Sep. 27, 2017.

*Primary Examiner* — Spencer E. Bell
(74) *Attorney, Agent, or Firm* — Lorenz & Kopf, LLP

(57) ABSTRACT

The present disclosure especially relates to a method, carried out by one or more devices, said method comprising: non-destructively determining structural information that is characteristic of at least part of the structure of a textile (202); ascertaining at least one treatment parameter of the textile (202) at least partly on the basis of said structural information; and outputting or initiating output of the at least one treatment parameter.

20 Claims, 4 Drawing Sheets

(51) Int. Cl.
  *G06T 7/60* (2017.01)
  *D06F 39/00* (2020.01)
  *D06F 33/00* (2020.01)
  *D06F 34/18* (2020.01)
  *D06F 35/00* (2006.01)

(52) U.S. Cl.
  CPC ........... *G01N 29/04* (2013.01); *G06K 9/6267* (2013.01); *G06T 7/60* (2013.01); *H04N 13/204* (2018.05); *D06F 35/005* (2013.01); *D06F 2202/10* (2013.01); *D06F 2204/02* (2013.01); *D06F 2204/04* (2013.01); *D06F 2204/10* (2013.01); *D06F 2214/00* (2013.01); *G01N 2291/0237* (2013.01); *G06K 2209/01* (2013.01); *G06T 2207/10028* (2013.01); *G06T 2207/30124* (2013.01)

(56) References Cited

U.S. PATENT DOCUMENTS

| | | |
|---|---|---|
| 2001/0042391 A1 | 11/2001 | Wobkemeier |
| 2004/0249843 A1 | 12/2004 | Damrath |
| 2006/0190266 A1* | 8/2006 | Tanigawa .............. D06F 34/18 704/273 |
| 2007/0248246 A1 | 10/2007 | Cherkassky et al. |
| 2008/0078035 A1 | 4/2008 | Haught et al. |
| 2010/0205823 A1 | 8/2010 | Ashrafzadeh et al. |
| 2014/0326067 A1* | 11/2014 | Chanda ................... G01N 9/30 73/32 R |
| 2014/0352078 A1* | 12/2014 | Leitert .................. D06F 34/18 8/137 |
| 2016/0224860 A1 | 8/2016 | Koven |

* cited by examiner

METHOD FOR ASCERTAINING TREATMENT PARAMETERS OF A TEXTILE BY MEANS OF STRUCTURAL INFORMATION

CROSS-REFERENCE TO RELATED APPLICATION

This application is a U.S. National-Stage entry under 35 U.S.C. § 371 based on International Application No. PCT/EP2017/067337, filed Jul. 11, 2017 which was published under PCT Article 21(2) and which claims priority to German Application No. 10 2017 209 865.1, filed Jun. 12, 2017, and which further claims priority to German Application No. 10 2016 212 979.1, filed Jul. 15, 2016, which are all hereby incorporated in their entirety by reference.

TECHNICAL FIELD

The present disclosure relates to methods and devices by which, by way of nondestructively determining structural information indicative of at least a portion of the structure of a textile, at least one treatment parameter of the textile is ascertained, on the basis of the structural information at least in part.

BACKGROUND

During use, textiles have to regularly undergo treatment such as a cleaning treatment or ironing. The user generally manually selects a particular type of treatment having corresponding treatment parameters. In this case, treatment parameters may in particular be the cleaning agent type, cleaning temperature and the ironing temperature. The structure of the textile is generally identified by employing the optical appearance for the human eye. The optimal treatment parameters for a treatment are often ascertained according to the user's experience and on the basis of markings on the textile, for example by employing textile care symbols on a label attached to the textile.

In this case, textiles comprise in particular clothing, curtains or bedding. Clothing and bedding include for example shirts, t-shirts, dresses, jackets, pullovers, trousers, blankets, covers and slips. The textiles may comprise various materials, for example natural fibers, synthetic fibers or further materials such as leather.

However, during selection of the textile treatment by the user, incorrect identification of the structure of the textile may lead to incorrect treatment. For example, textiles are subjected to unsuitable cleaning treatments or are ironed under incorrect conditions; in particular, the temperature during treatment is selected so as to be too high or a cleaning agent is used that is damaging for the structure of the textile. This may lead to increased wear of the material of the textile or even destruction of the textile. CN 204097748 U discloses a textiles recognition device comprising a code scanner and a processor. Bar codes or two-dimensional codes are fastened to the textiles and can be read in via the code scanner. In this case, the device determines, from the scanned information, a specific program for cleaning the textile using a washing machine. A corresponding program can then be executed automatically by the washing machine.

A problem in this case, however, is that every textile must be provided with a corresponding marking or a corresponding code, in a manner similar to commercially available textile care symbols. As a result, the outlay for producing the textiles is increased and the attached labels or marking are often undesired for aesthetic reasons. Moreover, not all textiles comprise corresponding markings. Labels can also be removed, as a result of which the structure of the corresponding textiles again cannot be easily identified. Accordingly, the risk of incorrect treatment remains.

Older textiles may also already have signs of wear and for example what are known as pilings, which result from fibers detaching from the textile composite and appearing on the surface of the textile in the form of knots. Treatment processes may then have to be adjusted according to the material wear in order to prevent further, increased material wear or for example also to remove pilings in order to restore the appearance of the textile. However, the conventional markings such as textile care symbols do not give any indication regarding requirements of this kind that change on account of wear.

Against the background of the described prior art, the object of the present disclosure is therefore that of reducing or preventing the above-described problems at least in part, i.e. facilitating identification of the structure of the textile and recommending an optimal treatment for the textile in accordance with the structure.

BRIEF SUMMARY

Method, devices, and systems for ascertaining treatment parameters of a textile by employing structural information of the textile are provided herein. In an embodiment, a method, carried out by one or more devices, includes nondestructively determining structural information that is characteristic for at least a portion of a structure of a textile. At least one treatment parameter of the textile is ascertained at least in part on the basis of the structural information. The at least one treatment parameter is then output or the output is triggered by the one or more devices.

BRIEF DESCRIPTION OF THE DRAWINGS

The present disclosure will hereinafter be described in conjunction with the following drawing figures, wherein like numerals denote like elements, and wherein.

DETAILED DESCRIPTION

Figure 1:
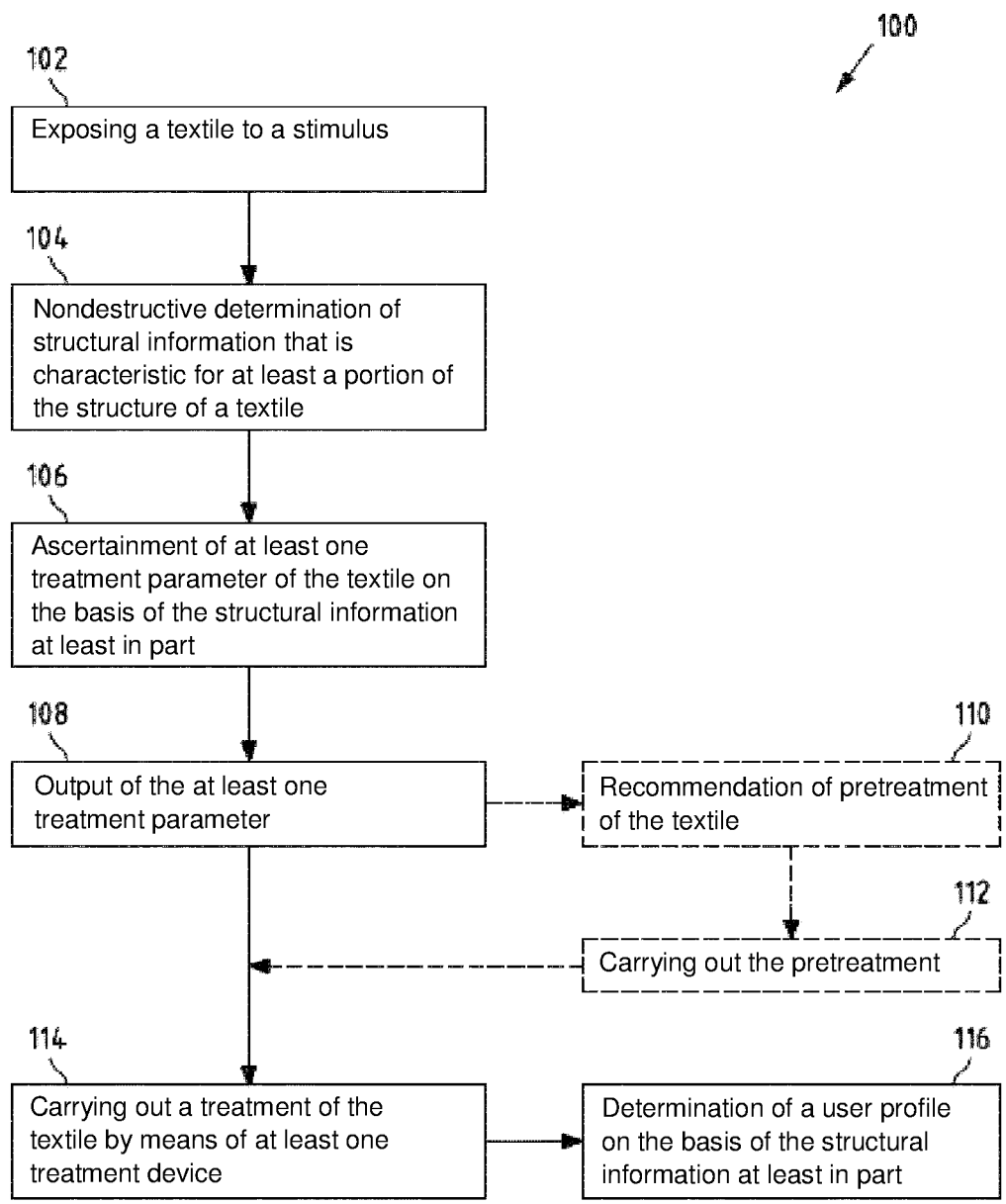
FIG. 1 is a flow diagram of an embodiment of a method.

The following detailed description is merely exemplary in nature and is not intended to limit the disclosure or the application and uses of the subject matter as described herein. Furthermore, there is no intention to be bound by any theory presented in the preceding background or the following detailed description.

A first aspect of the present disclosure describes a method that is carried out by one or more devices, the method comprising: nondestructively determining structural information characteristic for at least a portion of the structure of a textile; ascertaining at least one treatment parameter of the textile on the basis of the structural information at least in part; and outputting or triggering output of the at least one treatment parameter.

A second aspect of the present disclosure describes a device that is designed or that comprises corresponding features for carrying out and/or controlling a method according to the first aspect.

Devices of the method according to the first aspect are or comprise in particular one or more devices according to the second aspect.

An item of structural information that is characteristic for at least a portion of the structure of a textile is determined. In particular, according to the first aspect, a structure sensor or surface sensor is used, or, according to the second aspect, in particular a structure sensor is provided, which sensor is designed to provide structural information relating to a textile. In this case, the structure sensor may for example ascertain information relating to the shape, quality, appearance and composition of the textile and of the material of the textile.

The structural information is determined nondestructively. During nondestructive determination, the material and the structure are not or are only insignificantly influenced by the ascertainment, and in particular the appearance of the textile for the user does not change owing to the ascertainment of the structural information. For example, the reaction of the textile to a stimulus, for example a mechanical, optical or acoustic stimulus, is studied without the stimulus irreversibly influencing the textile. The ascertainment of the structural information, and in particular a structure sensor, may be based for example on mechanical scanning, an optical or acoustic measurement, chemical analysis, or a combination thereof. In contrast to invasive or destructive methods, which are based for example on removing a sample of the textile or on an invasive chemical reaction, the advantage of said nondestructive method is that the textile experiences little wear when the method is carried out.

On the basis of the structural information, at least one treatment parameter for the textile can be ascertained. The treatment parameter is in particular a recommendation for a specific treatment that is matched to the structure of the textile. For example, particularly gentle treatment of the textile may be the primary concern, such that the at least one treatment parameter ensures the greatest possible durability of the textile. Likewise, particularly intensive treatment of the textile may be desired, the at least one treatment parameter being optimized in view of the effect of the treatment of the specific structure, for example the effectiveness of a cleaning process. The at least one treatment parameter may also represent a recommendation of particularly energy-saving treatment.

The at least one treatment parameter is output, or the output thereof is prompted. For example, the at least one treatment parameter is shown to the user on a display feature, such that the user is for example provided, in particular visually and/or acoustically, with a recommendation for an optimal treatment for the textile. The user can then carry out the treatment.

The user may for example also be provided with a plurality of sets of treatment parameters, for example treatment parameters for particularly gentle, for particularly intensive and for particularly energy-saving treatments. The user may also be provided with various equivalent alternatives for possible treatment parameters. For example, the method comprises providing a plurality of treatment parameters, the user being able to make a selection, in particular by employing retrieving preferences, for example.

Alternatively or in addition, the at least one treatment parameter may be forwarded to a treatment device. For example, the at least one treatment parameter may be delivered to a treatment device which assumes the corresponding treatment parameter as a preliminary setting, and the user merely needs to start the treatment device. It is likewise conceivable for the treatment device to carry out the cleaning treatment automatically when the at least one treatment parameter is output. The cleaning device may for example comprise a dosing device for cleaning agent in order to automatically provide the cleaning agent type and cleaning agent amount in accordance with the recommended treatment. As a result, the user-friendliness of the method is thus improved.

In an embodiment of the method according to the first aspect, the structural information is indicative of material structure, material color, material type, material distribution, material wear of the textile, or a combination thereof.

The material structure of the textile is understood in particular as the type and/or form of a woven fabric, a knitted fabric or non-woven fabric and/or fiber web. The corresponding structural information may in particular be characteristic for the type of the braiding of fibers, and the way in which said braiding was produced, for example by employing weaving, stitching or knitting, or characteristic for a non-woven fabric. In this case, the structural information may include a braiding pattern or a thread interlacing pattern and thread binding. The structural information may in particular include the thread count, fiber strength, fiber length, fiber fineness and/or fiber orientation. The material structure of the textile has a direct influence on the requirements for the treatment of the textile; for example, a non-woven fabric may have different requirements for cleaning treatment compared with a stitched or woven structure.

The material color may be indicative of one or more colors of the textile. For example, the structural information indicates average dyeing, a color distribution and/or measure for the homogeneity of the color distribution. For example, the structural information contains values in a color space such as an RGB color space and/or an L*a*b* color space. In particular, a color reference, such as a color card, which is incorporated in the structural information, is used for ascertaining the structural information indicative of the color of the textile. The ascertainment of the structural information indicative of the color of the textile may comprise white balancing, for example using a reference such as a gray card which is incorporated in the structural information. The ascertainment of the structural information indicative of the color of the textile may in particular comprise aspects of the method described in WO2016/126470 A1, the subject matter of WO2016/126470 A1 being incorporated in the disclosure of the present application.

In particular, the structural information contains a measure for the gloss of the structure of the textile, which is exemplified by the reflection of the surface of the textile, in particular by the diffuse reflection of the surface. For example, the structural information comprises an angular dependency of the reflectivity of the surface of the textile. The structural information in particular comprises a measure for the gloss of the structure of the textile at a plurality of points on the surface, in particular at clean and contaminated points.

The material type is understood in particular to be the composition of at least a portion of the material of the textile. For example, the structural information is indicative of natural fibers, synthetic fibers or natural materials such as wool or leather in the textile. The material type also has a significant influence on optimal treatment of the textile, for example cleaning treatment or ironing.

The material distribution of the textile makes it possible for example to identify whether the textile comprises a mixed fabric including different fiber types or fiber materials, and/or whether sub-regions of the textile are manufactured from a different material. In this case, it is possible to identify the ratio of the different materials to one another, for example a density ratio, mass ratio or surface area ratio. Furthermore, the structural information may contain the type and number of binding points, for example seams, welds or adhesion points.

The structural information indicative of the material wear makes it possible in particular to ascertain whether pilings, cracks, holes, wear or other structural damage is present on the textile. In particular in the case of pilings, which result from fibers detaching from the textile composite and appearing on the surface of the textile in the form of knots, the type, shape, size or height, number and/or distribution of the material wear can be ascertained. The ascertainment of at least one treatment parameter on the basis of the material wear allows for the treatment processes to be adjusted according to the material wear in order to prevent further, increased material wear or for example also to remove pilings in order to restore the appearance of the textile.

In a further embodiment of the method according to the first aspect, the structural information is indicative of the presence and/or type of fasteners, coating material and/or appliqué patterns in and/or on the textile.

Fasteners on the textile are understood in particular to be zippers, Velcro fasteners, buttons or similar arrangements which are designed in particular to establish a connection between portions of the textile by employing interlocking, and which may be designed so as to be releasable.

The textile may comprise one or more coating materials; in particular the fibers are coated, or a coating is applied to the structure of the material of the textile, for example to the woven fabric. The coating may for example be a functional layer such as a protective layer or sealing layer, or may change the visual appearance or the feel of the textile.

Textiles, in particular clothing, may further comprise appliqué patterns such as imprints, sequins, lace, patches or the like, which can also be exemplified using the structural information. Likewise, functional textiles may comprise functional elements as appliqué patterns, or electronic elements may be arranged in the textile or on the surface of the textile.

If the structural information is indicative of such fasteners, coatings and/or appliqué patterns on the textile, care may also be taken, during treatment, to preserve the corresponding elements.

Wear of such fasteners, coatings and/or appliqué patterns during treatment can be reduced, and for example detachment of coatings or appliqué patterns can also be prevented. In a further embodiment of the method according to the first aspect, the at least one treatment parameter is indicative of a recommendation of pretreatment, a cleaning treatment and/or a final treatment of the textile.

In this case, pretreatment may comprise pre-cleaning, application of pretreatment agents, or a particular arrangement of the textile. For example, at least one treatment parameter specifies pre-cleaning or a prewash, in particular softening the textile in a particular solution, or a pre-cleaning program of a cleaning device. Different pretreatment agents may be provided for manual or automatic application; for example, application of a stain remover or a bleaching agent is specified. Furthermore, an arrangement of the textile can be specified in particular in that the textile is to be rotated "to the left" or arranged in a further device, such as a washing bag, prior to the treatment itself. Furthermore, the pretreatment may also comprise closing the fasteners; for example, the user may receive a notification to close a zipper for a subsequent treatment.

As a treatment of the textile it may be provided, for example, for the textile to be dyed or to undergo care treatment. For example, a dyeing recommendation may be ascertained on the basis of the structural information, according to the at least one treatment parameter the coloring of the textile being refreshed or changed by employing dyeing.

In an advantageous embodiment of the method according to the first aspect, the treatment comprises cleaning treatment, in particular washing treatment, carried out in a cleaning device, for example a washing machine.

The washing machine may be provided in various embodiments. A distinction is made between toploaders, in which the loading hatch is on the top, and front-loaders, in which a porthole functions as a loading hatch on the front. The advantage of the toploader is that the sealing of the door can be designed more simply, and the drum can be supported by rolling bearings on two sides. A toploader can also be installed in very small spaces where there is not enough space for opening a front door. A front-loader, in contrast, provides space on the top, e.g. for a tumble dryer or for a work surface, and is therefore sometimes installed in a kitchen unit instead of a floor unit.

The American toploaders always have a rotating drum and mixing elements (agitator or discs), it being possible for the mixing elements to move in or counter to the direction of rotation of the drum. The machines may comprise a suds recirculation mechanism and spraying devices for the suds. In principle, a distinction is made between deep fill and HE toploaders. Deep fill toploaders operate having a specified water level, and therefore do not have a load recognition feature. HE machines generally comprise a load recognition feature and control the water amounts in accordance therewith. In general, the machines do not have any installed heating feature, but are connected to hot and cold water.

In an embodiment, the at least one treatment parameter is indicative of a cleaning agent type, a cleaning agent amount, a cleaning temperature, a cleaning device type, settings of a cleaning device, or a combination thereof.

Cleaning agents are used for example domestically for cleaning various objects. For example, for washing machines, a cleaning agent, for example a washing agent, is used for cleaning textiles. However, a cleaning agent should also be understood as a cleaning aid or cleaning additive, such as a bleaching additive, a fabric softener or laundry starch. A cleaning agent may furthermore be a liquid, a disperse system, for example a gel or foam, or a solid, in particular a tablet, powder or granule. The cleaning agents mentioned can also be used for pretreatment or final treatment of the textile.

A cleaning agent may for example comprise one or more components from the group of components comprising surfactants, alkalis, building agents, graying inhibitors, optical brighteners, enzymes, bleaching agents, soil-release polymers, fillers, softeners, scents, dyes, care agents, acids, starches, isomalt, sugar, cellulose, cellulose derivatives, carboxymethylcellulose, polyetherimide, silicone derivatives and/or polymethylimines.

A cleaning agent may furthermore comprise one or more constituents. Said constituents include, but are not restricted to, the group including bleach activators, chelating agents, building agents, electrolytes, non-aqueous solvents, pH adjusters, perfume carriers, fluorescers, hydrotrypes, silicone oils, bentonites, antiredeposition agents, shrinkage prevention agents, anti-crease agents, dye transfer inhibitors, antimicrobial active ingredients, germicides, fungicides, antioxidants, preservatives, corrosion inhibitors, antistatic agents, bitters, ironing aids, phobing or impregnation agents, stabilizing or anti-slip agents, and/or UV absorbers.

The at least one treatment parameter may represent the cleaning agent type and thus be indicative of the composition of the recommended cleaning agent. If, for, example a certain proportion of wool is contained in the structure of the textile, or appliqué patterns are present on the textile, the user may be recommended to use correspondingly gentle cleaning agents.

The at least one treatment parameter may represent the cleaning agent amount and in particular specify an absolute amount of the cleaning agent. The at least one treatment parameter can also indicate a relative amount of the cleaning agent, for example based on the mass of the textiles to be cleaned or a bath ratio or a cleaning agent amount based on a water volume to be used for cleaning.

A treatment parameter representative of the cleaning temperature can specify a temperature for cleaning that is optimal for the particular structure of the textile, in particular in combination with a cleaning agent type. In this case, the cleaning temperature can be high enough to ensure cleaning of the textile that is as thorough as possible, and at the same time be kept low in view of energy use and care of the textile.

A cleaning device is intended to be understood in particular to be a washing machine, in particular an automatic domestic washing machine. In this case, a treatment parameter may specify a particular type of cleaning device of this kind. It is also conceivable for the treatment parameter to specify cleaning treatments to be carried out manually at least in part, for example a handwash. The at least one treatment parameter may also comprise settings of a cleaning device, for example a program of an automatic domestic washing machine or a sequence of programs of this kind. The duration of the treatment can also be provided by the treatment parameter, in order to achieve particularly gentle cleaning of the textile.

The recommendation of the treatment parameter for a final treatment may for example relate to drying or smoothing, in particular ironing of the textile. In this case, the at least one treatment parameter may specify inter alia the treatment temperature, treatment length and/or a treatment mode. A final treatment is carried out for example after the cleaning treatment. It is likewise possible to carry out final treatments such as drying or smoothing independently of a cleaning treatment.

As a result, the at least one treatment parameter indicative of a recommendation of pretreatment, a cleaning treatment and/or a final treatment of the textile can make it significantly easier for the user to identify the structure of the textile and the treatment thereof.

In particular in the case of textiles which do not have any markings for the treatment thereof, or in the case of worn textiles, a treatment that is optimal in view of caring for the material of the textile may be recommended by employing the method.

In a further embodiment, the method furthermore comprises: carrying out a treatment of the textile or prompting said treatment to be carried out in accordance with the at least one ascertained treatment parameter by employing at least one treatment device, in particular a cleaning device.

In a further embodiment of the method according to the first aspect, the structural information is determined before, during and/or after treatment of the textile. Determination before the treatment makes it possible for example for the user to be provided with a recommendation relating to the treatment parameters to be used before a cleaning treatment that is to be carried out.

In the case of determination of the structural information during treatment, the treatment may be carried out dynamically for example, i.e. a treatment device may adapt, during the treatment, to the structure currently to be treated of a sub-region of the textile, in particular by employing the treatment parameters being ascertained continuously. For example, an ironing device adapts the treatment parameters, for example the temperature, to the structure of the surface region of the textile currently being ironed, during movement over the surface of the textile.

Determination of the structural information after treatment makes it possible, for example, for the result or the effectiveness of a treatment to be ascertained and checked. In a subsequent embodiment of the method according to the first aspect, at least one optical sensor element is used for determining the structural information. Accordingly, the device according to the second aspect may comprise a structure sensor or surface sensor which comprises at least one optical sensor element.

An optical sensor element makes it possible to ascertain the appearance of the textile and the structure thereof using the image information, for example by employing values of a spatially resolved intensity distribution with or without color resolution. In this case, the optical sensor element may make it possible to identify the structure and may in particular provide an image resolution that exceeds that of the human eye, for example in terms of the energy resolution, the spatial resolution and/or in view of the wavelength range to be taken into account.

In this case, an optical sensor is understood as a sensor which can ascertain an intensity of incident radiation, in particular electromagnetic radiation, in the visible range and optionally beyond. The optical sensor is in particular designed to provide a spatial resolution and/or color information relating to the radiation incident in the sensor. The optical sensor may comprise an image sensor, in particular a digital image sensor. In order to ascertain the incident radiation, in particular at least one semiconductor element, diodes, CCD elements, for example a Bayer sensor, or CMOS elements, for example a sensor of the Foveon X3 type, may be used. The optical sensor may contain optical filters and in particular a spectrometer. Further optical elements such as lenses and/or filters, for example an external monochromator, may be provided.

According to an embodiment, the structural information is representative of spectral portions of a spectral image. The spectral portions may be within the visible range. If, according to a further embodiment of the method, the structural information is representative of spectral portions of a spectral image, at least one of the spectral portions being outside the visible energy range, the structure of the textile may be incorporated with an increased level of accuracy in the ascertainment of the treatment parameters. Since non-visible spectral portions are taken into account, different structures of textiles can also be identified, even though said structures cannot be distinguished by the naked eye. In order to ascertain spectral portions of the spectral image, it is possible in particular to carry out balancing using a sensitivity spectrum of the structure sensor, for example on the basis of specified settings or by employing comparison with a reference.

In particular, the structural information is representative of spectral portions of a spectral image in the ultraviolet energy range. Spectral portions in the infrared energy range can likewise be taken into account. The structural information is in particular representative of spectral portions of a spectral image from the infrared energy range to the ultraviolet energy range, for example at least for spectral portions of a spectral image having wavelengths of from about 1,400 nm to about 315 nm, preferably for wavelengths of from about 3,000 nm to about 280 nm, more preferably for wavelengths of from about 5,000 nm to about 200 nm. The structural information is in particular representative of spectral portions of a spectral image in the (near) infrared energy range, for example for wavelengths of from about 700 nm to about 2,400 nm, in particular from about 780 nm to about 2,000 nm, in particular up to about 1,450 nm.

It is also conceivable to use monochromatic sensors without color resolution. It is likewise possible to use sensors which are restricted to particular wavelength ranges, for example on the basis of at least one photodiode and/or at least one LED element.

In an embodiment of the method, the method furthermore comprises: carrying out referencing of the ascertainment of the structural information. For example, in order to ascertain spectral portions of the spectral image, in particular balancing may be made with a sensitivity spectrum, for example with reference to specified settings or by employing a comparison with a reference. The reference may in particular be provided as a card, for example in the form of a color card, gray card and/or a size measure that can be laid on the textile. Likewise, a reference may be attached in and/or on a treatment device. For example, a surface in the inside of the treatment device, such as the surface of a cleaning container, is provided with a reference. The reference may also be part of outer packaging of an agent for a washing, cleaning, care or dying process, e.g. in the form of an imprint, a removable portion of the packaging or as digital information, e.g. in the form of an electronic label.

In an embodiment, the optical sensor element provides a three-dimensional spatial resolution. A three-dimensional spatial resolution makes it possible to further increase the accuracy of the determination of the structure of the textile. It is conceivable for the same optical sensor or the same sensor assembly to use a plurality of recordings from different perspectives. Likewise, optical elements specifically designed for a three-dimensional resolution, such as attachment lenses or objectives, may be provided, or a 3D camera may be used. Additional optical elements, for example attachment lenses or objectives, may be arranged on conventional, substantially two-dimensional, optical sensors, for example digital cameras or cameras integrated in mobile appliances. As a result, pre-existing devices can also be retrofitted for the purpose of a three-dimensional resolution. The three-dimensional resolution makes it possible to more thoroughly determine for example the shape and arrangement of the woven fabric, the knit or the non-woven fabric, and to thus achieve more comprehensive and more accurate structural information.

The structural information in particular comprises one or more parameters, an item of size information, for example of a spatial extent or of the volume of the textile. In particular, the dimensioning of the structure of the textile, for example the fiber strength, fiber density, stitch size, stitch density, amount of wear such as pilings, can also be determined. In particular, the dimensioning is determined in conjunction with a reference.

The structural information in particular comprises a measure for the roughness of the surface, for example in conjunction with a three-dimensional spatial resolution. The measure for the roughness may for example comprise the average roughness $R_A$, the average roughness depth $R_z$ and/or the maximum roughness depth $R_{max}$. The structure of the textile can be further determined using the roughness. In particular, the roughness may also be an indication of the degree of wear of the textile.

One or more references may also be used for ascertaining the structural information by employing a structure sensor, in particular comprising an optical sensor element. The structure sensor may identify the references before, after and/or at the same time as the structural information. For example, a calibration card is used which comprises color references and/or size references. Acquisition of the calibration card thus makes it possible, for example, to more accurately determine the structural information relating to the color and the dimensions, in particular in the case of three-dimensional spatial resolution.

In a particularly simple embodiment, the at least one optical sensor element comprises at least one camera-like element and provides image information. Accordingly, digital cameras or cameras integrated in mobile appliances may be used for the method or may serve as at least one device for carrying out the method. In this case, attachments for a three-dimensional spatial resolution can be used on the camera-like element.

In an embodiment, the image information comprises at least two individual images of the textile. In this case, the individual images may represent a temporal sequence, for example one or more film sequences, or may also reproduce a variation in the position and perspective of the camera-like element. The accuracy of the structural information can be further increased thereby. In particular, as described above, a three-dimensional spatial resolution can be achieved using a plurality of individual images. The structure of the textile can likewise be captured from different sides, for example from the front, rear, outside and/or inside. In particular, contamination on the textile can also be identified from different sides.

In a further embodiment of the method according to the first aspect, the structural information of the textile comprises image information relating to lettering of a marking of the textile. A marking is understood in particular to be a label which is in particular attached to the textile. The marking may also be arranged on the structure of the textile itself, in part or completely. The marking is in particular indicative of parameters characteristic for the structure of the textile, in particular the material structure, material type, material distribution, color of the textile, material wear of the textile, type and/or shape of a woven fabric, a knitted fabric, non-woven fabric or fiber web, or a combination thereof. The marking is in particular indicative of parameters characteristic for a treatment parameter.

In this case, the marking comprises lettering. The lettering comprises in particular text characters and/or care symbols. In this case, care symbols may be standardized care symbols, for example care symbols according to the Ginetex standard. In particular, in this case lettering does not include codes, for example two-dimensional or three-dimensional barcodes. The structural information can thus be provided on the basis of a labeling which is in particular characteristic for the composition of the structure of the textile, for example a labeling according to German Textile Labeling Act (TKG) and/or a care instruction label which specifies preferred treatments for the textile.

The method according to the first aspect in particular comprises character recognition and/or classification of the lettering. For this purpose, one or more character recognition actions can be carried out, for example in an optical character recognition (OCR) method and/or an intelligent character recognition (ICR) method, in order to resolve the lettering of the marking. In particular, the structural information is processed by one or more filters, for example for setting brightness, contrast and/or color depth. The structural information may undergo classification for character recognition and/or for identifying care symbols, in particular in combination with a contextual analysis. This is helpful in particular in the case of markings on textiles, because the markings may already be influenced by the age of the textile and for example already faded or incomplete. Incomplete lettering can thus be completed using the contextual analysis. For example conventional lettering on labels on textiles can be recognized by employing character recognition, and therefore the textiles do not need to have special labels.

The ascertainment of the at least one treatment parameter in particular comprises correlation of the structural information. In particular, portions of the structural information can be correlated with one another. In this case, portions representative of image information of the structure of the textile, portions representative of spectral portions, in particular including the (near) infrared range, portions representative of image information of lettering on a marking, or combinations thereof, can be correlated with one another. For example, the type of woven fabric is ascertained by employing the image information and the material composition of the structure is determined by employing the spectral portions, and the corresponding parameters are compared with the evaluation of the image information of the marking.

In a further embodiment of the method, the structural information is representative of a hyperspectral image. Structural information representative of a hyperspectral image is understood in particular to mean that the structural information comprises, as an intensity distribution, intensity values in a plurality of channels for different energy intervals, at least two of the energy intervals adjoining or overlapping one another. In particular, a hyperspectral image can be distinguished from a multispectral image in that, although a multispectral image also comprises intensity values in a plurality of channels for different energy intervals, the energy intervals are mutually spaced, i.e. a multispectral image reproduces intensities of individual, mutually delimited energies. In contrast, a hyperspectral image in particular reproduces "neighboring" intensity values, in that at least two of the energy intervals adjoin or overlap one another. A hyperspectral image can thus reproduce a continuous spectrum at least in part. Structural information representative of a hyperspectral image is advantageous in particular in that information that is not visible to the naked eye and that is indicative of the composition of the contamination and/or the structure of the textile can also be identified.

In this case, the structural information may comprise values in at least about 20 channels, each channel representing an intensity for one energy interval. If values of the structural information are provided in at least about 20 channels, the resolution of the spectral image, and thus also the accuracy of the ascertainment of the at least one treatment parameter, can be improved. In particular, the structural information comprises at least about 20 channels to about 250 channels, making it possible to achieve more precise dependency of the treatment parameter on the composition of the contamination and/or on the structure of the textile. Using at least about 20 channels makes it possible to represent, in an item of structural information representative of a spectral image, in particular of a hyperspectral image, energy intervals that cannot be resolved by the human eye, which comprises just three channels in the visible range.

In a further embodiment of the method according to the first aspect, at least one acoustic sensor element is used for determining the structural information of the textile. The device according to the second aspect can accordingly comprise a structure sensor comprising at least one acoustic sensor element.

In this case, an acoustic sensor element can identify the sound emitted in the case of stimulus of the textile and can use said sound for determining structural information, allowing for nondestructive structure determination. In particular, the acoustic sensor element detects soundwaves of different frequencies or frequency ranges and uses said soundwaves in an evaluation of the structural information in order to ascertain the at least one treatment parameter. Advantageously, said frequencies or frequency ranges also include frequencies outside the audible range of from about 16 Hz to about 20 kHz, and are for example in the ultrasound range, such that the user is not affected by the emitted soundwaves. The acoustic sensor element can in particular measure sound on the textile in transmission and/or reflection.

The structure of the textile can be identified in a characteristic manner from an analysis of the ascertained sound, in particular from a frequency-dependent analysis. The analysis may in particular be based on values for the following physical variables, individually or in combination:
  sound particle velocity (or speed) v;
  sound energy flux (or sound particle velocity integrated over a surface) q;
  sound pressure p;
  sound impedance (or acoustic impedance) Z;
  sound velocity c, in particular direction-dependent sound velocity c in the structure of the textile; and
  displacement/amplitude of the sound.

According to an embodiment of the method according to the first aspect, the method furthermore comprises applying a processing algorithm to the ascertained structural information.

As a result, different structures of the textile can be better distinguished. For example, a conversion algorithm can be applied to the ascertained structural information. For example, the ascertained structural information (for example one or more items of image information) may be converted from a first representational space into a second representational space, for example from a first color space into a second color space. Examples for color spaces are for example an RGB color space or an L*a*b* color space. For example, the ascertained image information is converted from an RGB color space into an L*a*b* color space.

An RGB color space is to be understood as an additive color space which reproduces color perceptions by employing additive mixing of three primary colors (red, green and blue). An example for an L*a*b* color space is for example the CIELAB color space, which is standardized in EN ISO 11664-4 "Colorimetry—Part 4: CIE 1976 L*a*b* Colour space." An advantage here is that colors are defined, independently of the manner of their creation or reproduction technique, in the way in which they are perceived by a normal observer in standard light conditions (device independence and perception relatedness).

In order to ascertain the treatment parameters or to analyze the image information, it is possible in particular to evaluate color differences between pixels of one item of image information. For this purpose, in particular methods based on the color difference or the color spacing ΔE can be used. In particular, the ΔE is calculated in the CIELAB color space. Likewise, the brightness in the image information can be used for ascertaining the at least one treatment parameter.

In particular for frequency-dependent analysis of the structural information, processing comprising a Fourier transform analysis or similar mathematical methods may be carried out. In this case, the analysis can be used for particular frequencies or frequency ranges. The temporal dependency of the structural information can also be considered. In particular, in the case of frequency-dependent analysis, processing may comprise a short-time Fourier transform analysis, for example.

In an embodiment of the method, the ascertainment of the at least one treatment parameter comprises a comparison of the structural information with comparative values. Corresponding comparative values may be stored in a database. The structural information may undergo classification, the at least one treatment parameter being maintained or influenced by a result of the classification. Classification may for example be based on a comparison of the structural information with a database of already known structural information. Furthermore, the corresponding comparative values may be assigned particular treatment parameters.

The ascertainment of the treatment parameter may comprise one or more steps of feature extraction and/or feature balancing. Methods are used, for example, which correspond to those for evaluating biometric images.

In this case, the evaluation of the structural information or the ascertainment of the at least one treatment parameter can be carried out using the device which also comprises the structure sensor. For example, the structure sensor is arranged on a mobile appliance, a treatment device such as a cleaning device, or a container such as product packaging of treatment agents, for example packaging of a cleaning agent, and the same device also comprises an evaluation unit which carries out or prompts the ascertainment of the at least one treatment parameter.

The evaluation of the structural information or the ascertainment of the at least one treatment parameter can also be carried out by a further device which is connected, in particular by employing a communication system, to the device which comprises the structure sensor. A server may be provided for this purpose, which server carries out the evaluation or prompts further devices to carry out the evaluation. A sever of this kind is a database server for example. Examples of a database server include Microsoft SQL Server, Oracle Server and MySQL Server. The servers may for example be a part or a component of what is known as a computer cloud, which dynamically provides data processing resources for various users in a communication system. A computer cloud is understood in particular to be a data processing infrastructure according to the "National Institute for Standards and Technology" (NIST) definition for the term "Cloud Computing." An example of a computer cloud is a Microsoft Windows Azure Platform.

In a further embodiment of the method according to the first aspect, the method furthermore comprises exposing the textile to a stimulus. As a result, the ascertainment of the structural information by employing the structure sensor can be based on a defined stimulus. For example, for an optical sensor element, the textile is exposed to or illuminated by radiation by employing a light source, the radiation used having a particular intensity and/or particular spectral distribution. Such illumination of at least a portion of the textile ensures sufficient illumination of the textile, in particular for using an optical sensor element, irrespective of the external conditions. This can make it possible to ascertain the structural information, or can in any case improve the quality of the ascertainment, even in the event of poor external conditions, such as little daylight in a dark room.

Illumination is understood to mean that light is generated using an artificial light source, such that in particular (improved) visualization of the structure of the textile can take place. The illumination is achieved in particular by employing radiation which is in the visible range of the electromagnetic spectrum at least in part, for example radiation of which the wavelength covers at least a portion of the wavelength range from about 380 nm to about 780 nm. The stimulus can also comprise portions in the (near) infrared range and/or in the ultraviolet energy range. The wavelength range can furthermore be specifically adjusted to a structure sensor.

In particular for an acoustic sensor element, it is possible to provide for exposure to sound or a sound source, also having a defined intensity and frequency response. The stimulus may also have a particular temporal sequence, for example a stimulus signal is triggered at a specific time, is of a specific duration, and/or has a particular temporal progression of the intensity and the frequency response.

The duration of the stimulus may in particular be relatively short, i.e. less than one second. In the case of an optical stimulus, a flash light is used, for example. The duration of the stimulus can furthermore be less than about 0.1 seconds, in particular less than about 0.01 seconds.

In an embodiment of the device according to the second aspect, at least one stimulus feature and at least one structure sensor are arranged integrally on a device and are thus located on the same appliance, for example a mobile appliance. A combined arrangement of this kind increases the user-friendliness for the use of the device. A mobile appliance such as a smart pen may be provided, which appliance is detachably arranged on and/or in the treatment device and can communicate with the treatment device, for example via a cable and/or wirelessly. A mobile appliance of this kind may comprise one or more sensors.

In a further embodiment, the method furthermore comprises: determining a user profile on the basis of the structural information at least in part, in particular on the basis of a plurality of items of structural information, the ascertainment of the at one treatment parameter being based on the user profile at least in part.

A user profile which is adjusted to the textile structure in question can thus be set by employing the at least one output variable. In particular, a plurality of treatment parameters can be incorporated in a user profile within the meaning of a history of ascertained treatment parameters, such that future ascertainment processes can be based on the user profile at least in part. As a result, the ascertainment of the at least one treatment parameter can be designed adaptively and can be more accurately adjusted to the relevant requirements by employing the user profile. The ascertainment of the treatment parameter can be carried out more accurately in particular in view of the dependency on the structure of the textile.

For example, a user profile can be created with regard to textile structures that are frequently to be treated.

It is likewise conceivable for information regarding the effectiveness of the treatment to be incorporated in the user profile. For example, structural information can be ascertained again following cleaning treatment in order to investigate the effect of the cleaning treatment on the structure of the textile, in particular with respect to resulting wear. As a result, future treatments can be further optimized by employing the user profile.

Likewise, the user can assess the at least one treatment parameter after treatment, for example can assess a cleaning treatment, which assessment is incorporated in the user profile. As a result, it is possible to achieve personalized adjustment of the ascertainment of the treatment parameter.

In particular, the user profile may also be influenced by further user profiles of other people. For example, preferences and/or comparative values can be compared with those of other users or be introduced as a suggestion. Within the context of crowdsourcing of this kind, the evaluation of the structural information can be further optimized.

It is likewise possible for the ascertainment of the at least one treatment parameter to comprise machine learning, in particular when using a user profile. Thus, for example, the user profile can be determined on the basis of machine learning at least in part. Machine learning is understood to mean that an artificial system (for example a device according to the second aspect or a system according to the third aspect) learns from examples and can generalize said examples after the learning phase has ended. That is to say that the examples are not simply memorized, but instead patterns and laws in the learning data are identified. Various approaches can be taken for this purpose. For example, supervised learning, semi-supervised learning, unsupervised learning, reinforcement learning and/or active learning can be used, in particular in conjunction with deep learning methods. Supervised learning can take place for example by employing an artificial neural network (such as a recurrent neural network) or by employing a support vector machine. Unsupervised learning can also take place for example by employing an artificial neural network (for example an autoencoder). In this case, for example in particular the repeatedly obtained and/or ascertained structural information or the at least one treatment parameter are used as learning data.

In a further embodiment of the method, at least one of the devices for carrying out the method is a mobile appliance. In particular, communication can take place, via a communication system, between a mobile appliance, for example a smartphone, laptop, tablet, wearable device, smartwatch, smart pen or a camera, and at least one further device, for example a cleaning device, a device for a final treatment such as an ironing device, and/or a structure sensor. One of the devices may also be a cleaning robot. According to an embodiment, the device according to the second aspect comprises a communications interface. The communications interface is designed for wired or wireless communication for example. The communications interface is a network interface for example. The communications interface is preferably designed to communicate with a communication system. Examples for a communication system are a local network (LAN), a wide-area network (WAN), a wireless network (for example according to the IEEE 802.11 standard, the Bluetooth (LE) standard and/or the NFC standard), a wired network, a mobile radio network, a telephone network and/or the Internet. A communication system may comprise communication with an external computer, for example via an Internet link.

According to the second aspect of the present disclosure, an alternative device is also described, comprising at least one processor and at least one memory comprising computer program code, the at least one memory and the computer program code being designed to execute and/or to control at least one method according to the first aspect using the at least one processor. A processor is intended to be understood to be for example a control unit, a microprocessor, a micro control unit such as a microcontroller, a digital signal processor (DSP), an application-specific integrated circuit (ASIC) or a field programmable gate array (FPGA).

A device by way of example further comprises, for example, a feature for storing information, such as program memory and/or a main memory. A device by way of example as contemplated herein in each case further comprises, for example, a feature for receiving and/or transmitting information via a network such as a network interface. Devices by way of example as contemplated herein for example are and/or can be interconnected by employing one or more networks.

A device by way of example according to the second aspect is or comprises for example data processing equipment which is configured, in terms of software and/or hardware, to be able to execute the relevant steps of a method by way of example according to the first aspect. Examples of data processing equipment are a computer, a desktop computer, a server, a thin client and/or a portable computer (mobile appliance) such as a laptop computer, a tablet computer, a wearable device, a personal digital assistant or a smartphone.

According to the second aspect of the present disclosure, a computer program is also described, which computer program comprises program instructions which prompt a processor to execute and/or control a method according to the first aspect when the computer program is run on the processor. A program by way of example as contemplated herein may be stored in or on a computer-readable storage medium which contains one or more programs.

According to the second aspect of the present disclosure, a computer-readable storage medium is also described, which medium contains a computer program according to the second aspect. A computer-readable storage medium may be designed for example as a magnetic, electrical, electromagnetic, optical and/or other storage medium. A computer-readable storage medium of this kind is preferably a physical object (i.e. "tangible"), for example is designed as a data carrier device. A data carrier device of this kind is for example portable or permanently installed in a device. Examples of a data carrier device of this kind are volatile or non-volatile memories having random access (RAM), such as NOR flash memories, or having sequential access, such as NAND flash memories, and/or memories having read-only access (ROM) or write/read access. Computer-readable is intended to be understood to mean, for example, that the storage medium can be read (out) and/or written by a computer or data processing equipment, for example by a processor.

According to a third aspect of the present disclosure, a system is also described, which system comprises a plurality of devices, in particular a mobile appliance and a treatment device, which together carry out a method according to the first aspect.

A system by way of example according to the third aspect comprises a cleaning device by way of example and in addition a further device, for example a mobile appliance or a server for carrying out a method by way of example according to the first aspect.

In particular, the system according to the third aspect may further comprise at least one textile or a batch of textiles.

The embodiments of the present disclosure described above in this description by way of example should also be understood to be disclosed in all combinations with one another. In particular, embodiments by way of example should be understood to be disclosed with reference to the various aspects.

In particular, the above or following description of method steps according to preferred embodiments of a method is also intended to disclose corresponding features for carrying out the method steps by way of preferred embodiments of a device. Likewise, the disclosure of employing a device for carrying out a method step is also intended to disclose the corresponding method step.

Further preferred embodiments of the present disclosure by way of example can be found in the following detailed description of some embodiments of the present disclosure by way of example, in particular in conjunction with the drawings. However, the drawings should serve merely for illustrating, but not for determining, the scope of protection of the present disclosure. The drawings are not to scale and are intended merely to reflect the general concept of the present disclosure by way of example. In particular, features that are contained in the drawings should in no way be regarded as necessary constituents of the present disclosure.

Figure 2:
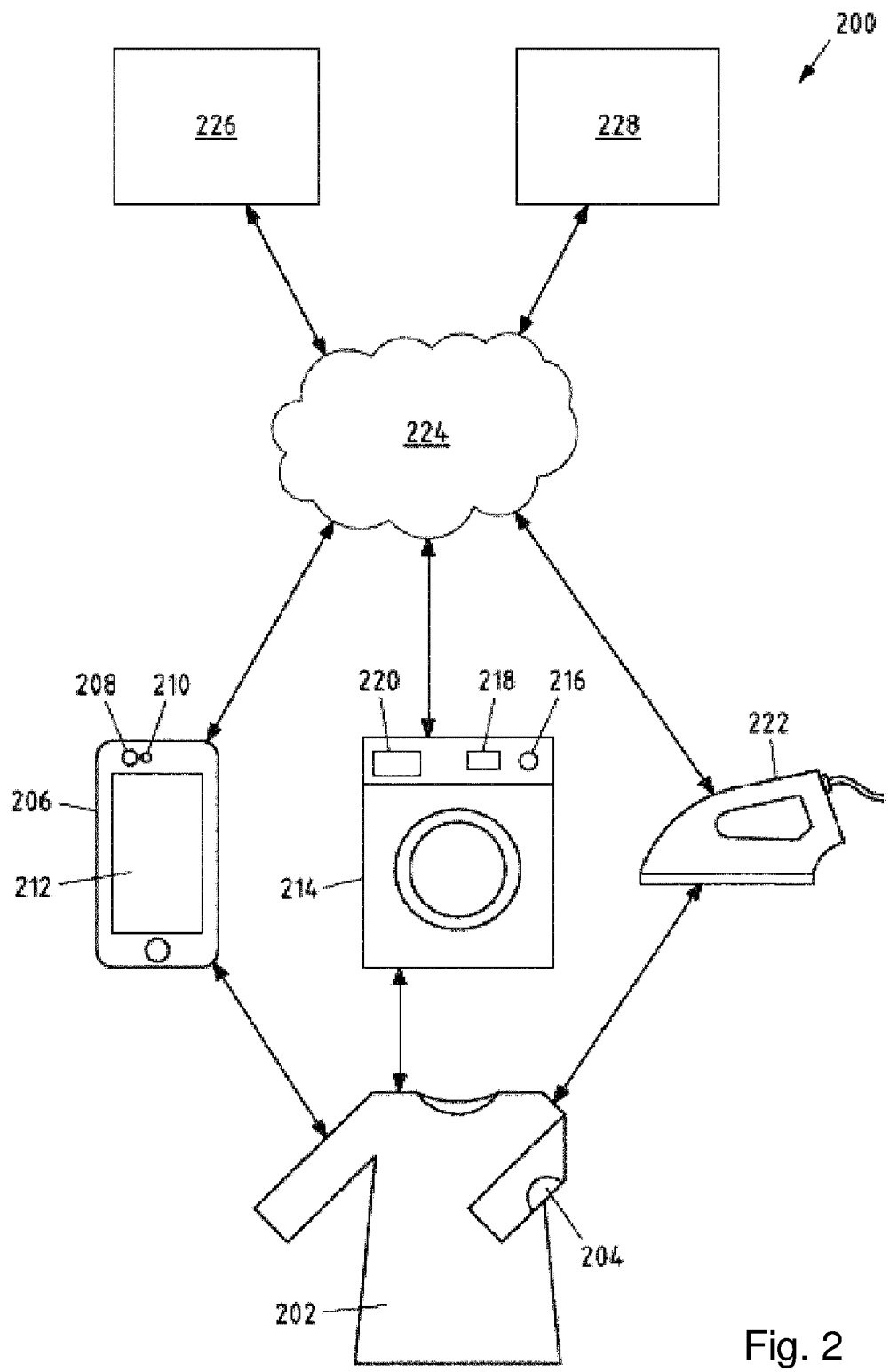
FIG. 2 is a schematic view of an embodiment of a device.

FIG. 1 is a flow diagram 100 of an embodiment of a method according to the first aspect, which method can be carried out by a device, for example one of the devices from FIG. 2.

In action 102, a textile, for example an item of clothing, is exposed to a stimulus. In particular, optical stimulation of the textile is carried out by employing exposure to radiation or illumination. In this case, light can be generated using an artificial light source, such that in particular improved visualization of the structure of the textile is brought about, for example by employing a flash light. Likewise, an optical stimulus can be provided by a natural light source, for example by daylight. Acoustic stimulation of the textile in the form of exposure to sound is furthermore possible.

In particular, nondestructive determination of structural information can be carried out in action 104, on the basis of said stimulus. In this case, the structural information is characteristic for at least a portion of the structure of a textile.

For example, during illumination of the textile, the radiation resulting from the surface of the textile is captured by an optical sensor element. In particular image information can be obtained as a result, preferably having a three-dimensional resolution, which image information is characteristic for the structure of the textile.

Likewise, an item of structural information of the textile can be obtained by at least one acoustic sensor element, in particular by employing an acoustic stimulus. In particular the sound particle velocity v, sound energy flux q, sound pressure p, sound impedance Z, sound velocity c, displacement of the sound, or a combination thereof is identified in order to obtain the structural information characteristic for the structure of the textile. In particular, direction-dependent variables are also identified in a direction-dependent manner.

In this case, the structural information may be indicative of the material structure, material type, material distribution and material wear of the textile. For example, the height, the shape and the number of pilings on the textile is identified using the structural information, for example three-dimensional image information. Furthermore, different material types, for example, wool, cotton and synthetic fibers, or material structures such as woven fabric or non-woven fabric can be exemplified by the structural information. It is likewise possible for the structural information to be indicative of the presence and of fasteners, such as zippers or buttons, of coating material, and of appliqué patterns on the textile.

In action 106, at least one treatment parameter of the textile is ascertained on the basis of the structural information at least in part. The treatment parameter may be indicative of a recommendation of pretreatment, for example an application of a pretreatment agent. Likewise, by way of example, an item of structural information characteristic for an appliqué pattern on the textile may indicate rotation of the textile "to the left" or a recommendation to arrange the textile in a washing bag.

The treatment parameter may furthermore be indicative of a recommendation for a cleaning treatment, such as for a cleaning agent type, a cleaning agent amount, a cleaning temperature, a cleaning device type, and settings of a cleaning device, such as a washing machine. If the structural information is characteristic for a woven fabric made of wool in the textile, for example a wool wash program at low temperatures using a special woollens detergent may be specified by the treatment parameters.

Likewise, the treatment parameter may be indicative of a final treatment of the textile. For example, the at least one treatment parameter indicates the temperature and a program for ironing or drying the textile.

The at least one treatment parameter is output in action 108 and is provided for example on a display feature, as a result of which the user has access to the recommendation regarding the treatment parameters of the textile. The user can be shown for example the material type and the material wear, as well as sets of treatment parameters for pretreatment, a cleaning treatment and a final treatment. This makes it easier for or allows the user to identify the structure of the textile and to ascertain the optimal treatment of the textile. The user can for example subsequently decide whether the treatment parameters should be taken on as recommended and carry out a treatment.

If a pretreatment is recommended in action 110 for example, the pretreatment can be carried out 112 automatically or manually. For example, the user rotates the textile "to the left," if appliqué patterns on the textile are indicated, or closes a zipper.

In action 114 a treatment is carried out, for example a cleaning treatment. In particular, the treatment parameters are output to at least one treatment device and serve as a preliminary setting. For example, a washing machine assumes a cleaning temperature and a cleaning program as a preliminary setting. The user then merely has to start the washing machine. At least one treatment device can also carry out a treatment automatically on the basis of the output treatment parameters. A cleaning device may for example also comprise a dosing device which automatically provides a cleaning agent type and a cleaning agent amount according to the output treatment parameters.

A treatment can also be carried out in action 114 by an ironing device. In this case, in particular the temperature of the ironing device is regulated according to the treatment parameters. The structural information is acquired continuously for example, such that the ironing device is operated according to the requirements of each sub-region of the textile, during movement over the textile.

In addition, a user profile can be determined in action 116, which profile is based on the treatment parameter at least in part. As a result, the ascertainment of the at least one treatment parameter can be designed adaptively and can be more accurately adjusted to the relevant requirements by employing the user profile.

FIG. 2 shows an embodiment of devices according to the second aspect or of a system 200 according to the third aspect.

A textile 202 in the form of an item of clothing has a particular structure; for example the textile 202 includes inter alia a woven fabric including wool, cotton or synthetic fibers. An appliqué pattern 204 is provided on the woven fabric of the textile 202 for example. In this case, the structure of the textile 202 may require a particular form of treatment, for example a particular form of cleaning or ironing.

An item of structural information of the textile 202, for example, can be ascertained using a mobile appliance 206, in this case a smartphone. A structure sensor 208, in particular an optical sensor or a camera-like element, is provided for this purpose. The structure sensor 208 identifies for example the radiation emitted from the surface of the textile, or an item of image information. In addition, a radiation source 210 is provided, which source is used to illuminate the surface of the structure of the textile 202. The mobile appliance 206 furthermore comprises a display element 212.

The determination of the structural information can also be provided by employing a structure sensor (not shown) in a cleaning device 214, in this case a washing machine. The structure sensor for example comprises an acoustic sensor element, the textile being stimulated by employing exposure to sound, and the structure sensor recording the reaction of the structure of the textile to said stimulus. The cleaning device 214 further comprises an operating element 216 for manual operation, a display element 218, and a dosing device 220 for a cleaning agent.

FIG. 2 furthermore shows an ironing device as the treatment device 222, which ironing device is used for final treatment or smoothing of the textile. The treatment device 222 may also comprise a structure sensor (not shown).

The structural information ascertained is received by a communication system 224 which is connected to the mobile appliance 206, the cleaning device 214 and the treatment device 222. An ascertainment device 226, which is designed to ascertain at least one treatment parameter that is dependent on the structural information of the textile 202, is furthermore connected to the communication system 224. The ascertainment device 226 may be designed as a separate device or for example also integrated in the mobile appliance 206, the cleaning device 214 and the treatment device 222.

Ascertaining at least one treatment parameter comprises for example using at least one processing algorithm, for example a conversion algorithm. For example, the image information of the optical structure sensor 208 undergoes image evaluation, in particular three-dimensional image evaluation. The ascertainment device 226 may also be connected to at least one further computer 228 by employing the communication system 224. The computer 228 may for example dynamically provide additional processing power for ascertaining the at least one treatment parameter and may also comprise a database containing comparative values.

The at least one treatment parameter is output, in particular on the display feature 212 of the mobile appliance 206 or the display feature 218 of the cleaning device 214. The user can then select a treatment according to the treatment parameters or the identified structure of the textile 202. For example, the cleaning device 214 assumes a cleaning temperature and a cleaning program as a preliminary setting. The dosing device 220 can automatically provide a cleaning agent type and a cleaning agent amount according to the output treatment parameters. The user then merely has to start the cleaning device 214 by employing the operating element 216 in order for optimal cleaning of the textile 202 to be carried out.

The device 200 can for example also regulate the temperature of the treatment device 222 during ironing of the textile 202, such that particularly gentle treatment of the textile 202 is ensured. In this case, the structure sensor of the treatment device 222 can ascertain the structural information continuously during the treatment, such that for example the temperature of the treatment device 222 can be set according to the structure of the sub-region of the textile currently treated.

Figure 3:
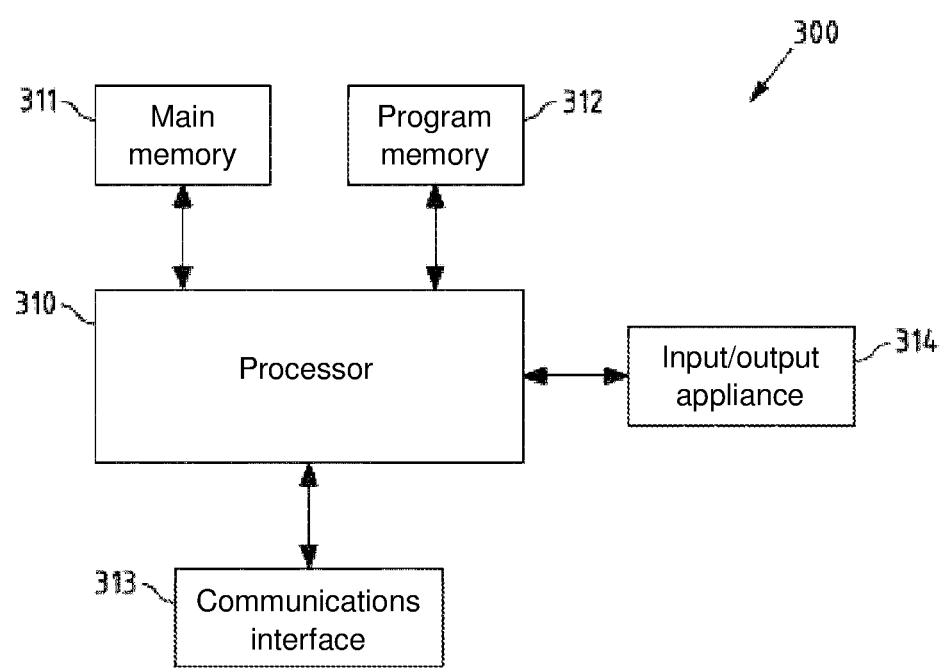
FIG. 3 is a block diagram of an embodiment of a device.

FIG. 3 is a block diagram of an embodiment of a device 300 which can in particular execute a method by way of example according to the first aspect. The device 300 is for example a device according to the second or a system according to the third aspect.

In this respect, the device 300 may for example be a computer, a desktop computer, a server, a thin client or a portable computer (mobile appliance) such as a laptop computer, a tablet computer, a personal digital assistant (PDA) or a smartphone. The device may for example fulfil the function of a server or a client.

The processor 310 of the device 300 is in particular designed as a microprocessor, micro control, microcontroller, digital signal processor (DSP), application-specific integrated circuit (ASIC) or field programmable gate array (FPGA).

The processor 310 executes program instructions which are stored in the program memory 312, and stores for example intermediate results or the like in a working or main memory 311. For example, the program memory 312 is a non-volatile memory such as a flash memory, magnetic memory, EEPROM memory (electrically erasable programmable read-only memory) and/or an optical memory. The main memory 311 is for example a volatile or non-volatile memory, in particular a memory having random access (RAM) such as a static RAM (SRAM), a dynamic RAM (DRAM), a ferroelectric RAM (FeRAM) and/or a magnetic RAM (MRAM).

The program memory 312 is preferably a local data carrier that is permanently connected to the device 400. Data carriers that are permanently connected to the device 300 are for example hard drives, which are installed in the device 300. Alternatively, the data carrier may for example also be a data carrier that can be separably connected to the device 300, for example a memory stick, a removable medium, a portable hard drive, a CD, a DVD and/or a disk.

The program memory 312 for example contains the operating system of the device 300, which system is loaded in the main memory 311 at least in part and is executed by the processor 310 when the device 300 is started. In particular, when the device 300 is started, at least a portion of the core of the operating system is loaded into the main memory 311 and executed by the processor 310. The operating system and device 300 is for example a Windows, UNIX, Linux, Android, Apple iOS and/or MAC operating system.

The operating system in particular makes it possible to use the device 300 for data processing. Said system for example manages operating features such as the main memory 311 and program memory 312, network interface 313, input and output appliance 314, provides fundamental functions inter alia by employing programming interfaces of other programs, and controls the execution of programs.

The processor 310 controls the communications interface 313 which may be a network interface for example and may be configured as a network card, network module and/or modem. The communications interface 313 is in particular designed to establish a connection between the device 300 and other devices, in particular by employing a (wireless) communication system, for example a network, and to communicate with said devices. The communications interface 313 can for example receive data (via the communication system) and forward said data to the processor 310, and/or receive and send (via the communication system) data from the processor 310. Examples for a communication system are a local network (LAN), a wide-area network (WAN), a wireless network (for example according to the IEEE 802.11 standard, the Bluetooth (LE) standard and/or the NFC standard), a wired network, a mobile radio network, a telephone network and/or the Internet.

Furthermore, the processor 310 may control at least one input/output appliance 314. The input/output appliance 314 is for example a keyboard, a mouse, a display unit, a microphone, a touch-sensitive display unit, a loudspeaker, a reader, a drive and/or a camera. The input/output appliance 314 can for example receive inputs from a user and forward said inputs to the processor 310, and/or receive and send information for the user from the processor 310.

Figure 4:
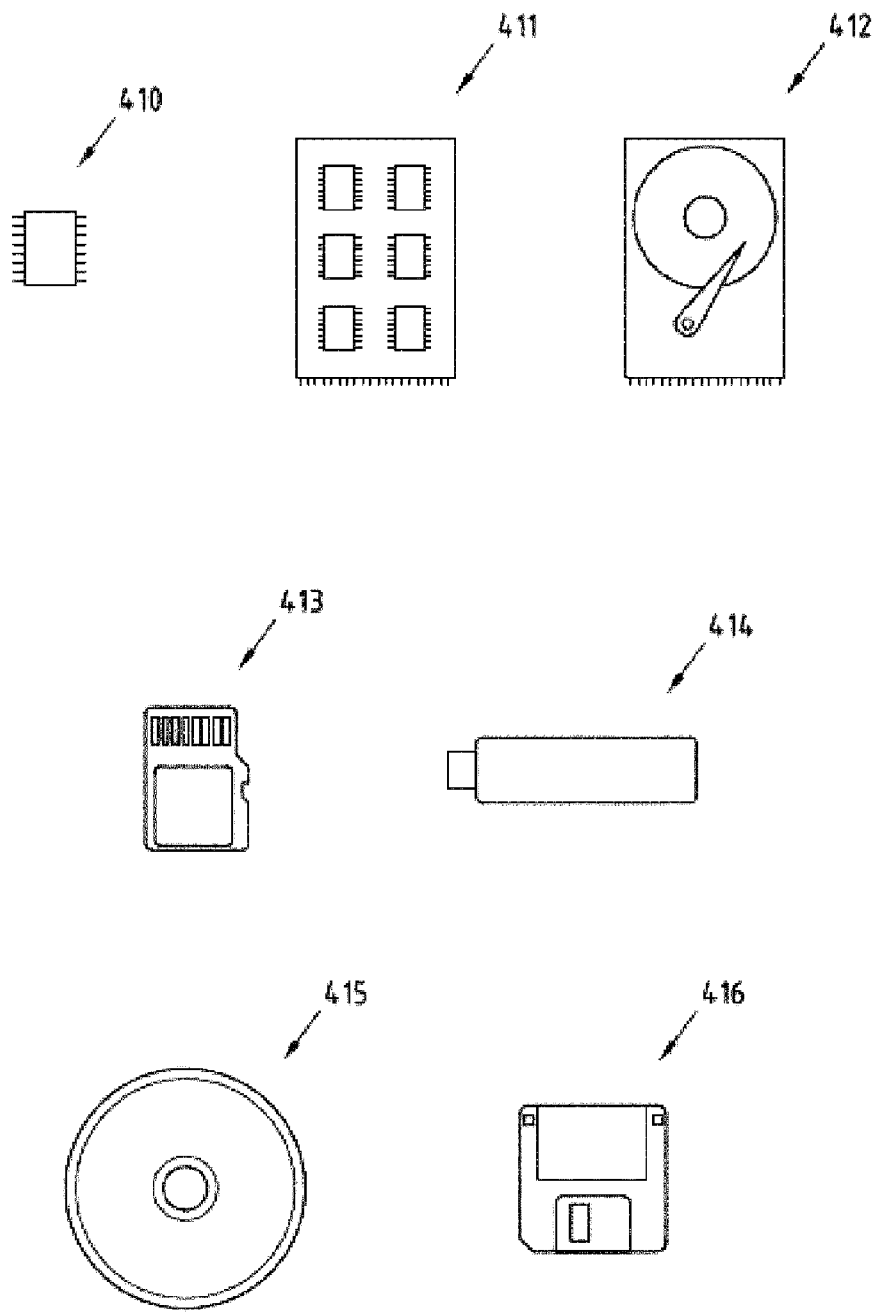
FIG. 4 shows various embodiments of a storage medium.

FIG. 4 finally shows various embodiments of storage media on which an embodiment of a computer program as contemplated herein may be stored. The storage medium may for example be a magnetic, electrical, optical and/or other storage medium. The storage medium may for example be part of a processor (e.g. the processor 310 of FIG. 3), for example a (non-volatile or volatile) program memory of the processor or a portion thereof (such as the program memory 312 in FIG. 3). Embodiments of a storage medium are a flash memory 410, an SSD hard drive 411, a magnetic hard drive 412, a memory card 413, a memory stick 414 (e.g. a USB stick), a CD ROM or DVD 415 or a disk 416.

The following embodiments are also to be understood as disclosed:

Embodiment 1

Method, carried out by one or more devices, comprising:
nondestructively determining structural information that is characteristic for at least a portion of the structure of a textile (202);
ascertaining at least one treatment parameter of the textile (202) on the basis of the structural information at least in part; and
outputting or triggering output of the at least one treatment parameter.

Embodiment 2

Method according to embodiment 1, wherein the structural information is indicative of material structure, material type, material distribution, material wear of the textile (202) or a combination thereof.

Embodiment 3

Method according to embodiment 2, wherein the structural information is indicative of the height, the shape and/or the number of pilings on the textile (202).

Embodiment 4

Method according to any of embodiments 1 to 3, wherein the structural information is indicative of the presence and/or type of fasteners, coating material and/or appliqué patterns (204) in and/or on the textile (202).

Embodiment 5

Method according to any of embodiments 1 to 4, wherein the at least one treatment parameter is indicative of a recommendation of pretreatment, a cleaning treatment and/or a final treatment of the textile (202).

Embodiment 6

Method according to embodiment 5, wherein the at least one treatment parameter is indicative of a cleaning agent type, a cleaning agent amount, a cleaning temperature, a cleaning device type, settings of a cleaning device (214), or a combination thereof.

Embodiment 7

Method according to any of embodiments 1 to 6, the method further comprising:
carrying out a treatment of the textile (202) or prompting said treatment to be carried out in accordance with the at least one ascertained treatment parameter by employing at least one treatment device (222), in particular a cleaning device (214).

Embodiment 8

Method according to any of embodiments 1 to 7, wherein the structural information is determined before, during and/or after a treatment of the textile (202).

Embodiment 9

Method according to any of embodiments 1 to 8, wherein at least one optical sensor element is used for determining the structural information of the textile (202).

Embodiment 10

Method according to embodiment 9, wherein the optical sensor element provides a three-dimensional spatial resolution.

Embodiment 11

Method according to either embodiment 9 or embodiment 10, wherein the at least one optical sensor element comprises at least one camera-like element (208) and provides image information about the textile (202).

Embodiment 12

Method according to embodiment 11, wherein the image information comprises at least two individual images of the textile (202).

Embodiment 13

Method according to any of embodiments 1 to 12, wherein the structural information of the textile (202) comprises image information of lettering of a marking of the textile (202) and in particular character recognition and/or classification of the lettering is carried out.

Embodiment 14

Method according to any of embodiments 1 to 13, wherein at least one acoustic sensor element is used for determining the structural information of the textile (202).

Embodiment 15

Method according to any of embodiments 1 to 14, the method further comprising:
exposing the textile (202) to a stimulus, in particular exposure to radiation and/or sound.

Embodiment 16

Method according to any of embodiments 1 to 15, the method further comprising:
determining a user profile on the basis of the structural information at least in part, in particular on the basis of a plurality of items of structural information,
wherein the ascertainment of the at least one treatment parameter takes place on the basis of the user profile at least in part.

Embodiment 17

Method according to any of embodiments 1 to 16, wherein at least one of the devices for carrying out the method is a mobile appliance (206).

Embodiment 18

Device that is designed or that comprises corresponding features for carrying out and/or controlling a method according to any of embodiments 1 to 17.

Embodiment 19

Device comprising at least one processor (310) and at least one memory (311, 312) comprising computer program code, wherein the at least one memory (311, 312) and the computer program code are designed to execute and/or to control at least one method according to any of embodiments 1 to 17 using the at least one processor (310).

Embodiment 20

Computer program that comprises program instructions which prompt a processor (310) to execute and/or control a method according to any of embodiments 1 to 17 when the computer program is run on the processor (310).

Embodiment 21

Computer-readable storage medium containing a computer program according to embodiment 20.

Embodiment 22

System, comprising:
a plurality of devices (206, 214, 222, 224, 226, 228), in particular at least one mobile appliance (206) and a treatment device (214, 222) which together carry out a method according to any of embodiments 1 to 17.

The embodiments of the present disclosure described in this specification and the optional features and properties set out in relation thereto in each case should also be understood to be disclosed in all combinations with one another. In particular, unless explicitly indicated otherwise, the description of a feature included in one embodiment is not intended to be understood, in the present case, to mean that the feature is necessary or essential for the functioning of the embodiment. The sequence of the method steps set out in this specification in the individual flow diagrams is not essential; alternative sequences of the method steps are conceivable. The method steps can be implemented in various manners; for example, implementation in software (by employing program instructions), hardware, or a combination of the two is conceivable for implementing the method steps.

In the claims, terms used such as "comprise," "have," "include," "contain" and the like do not exclude further elements or steps. The wording "at least in part" includes both the case of "in part" and the case of "completely." The wording "and/or" is intended to be understood such that both the alternatives and also the combination is intended to be disclosed; i.e. "A and/or B" means "(A) or (B) or (A and B)." The use of the indefinite article does not exclude a plurality. A single device can execute the functions of a plurality of units or devices mentioned in the claims. Reference signs stated in the claims are not to be considered to limit the features and steps used.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Method, carried out by one or more devices, comprising:
nondestructively determining structural information that is characteristic for at least a portion of a structure of a textile;
ascertaining at least one treatment parameter of the textile at least in part on the basis of the structural information; and
outputting or triggering output of the at least one treatment parameter using the one or more devices
wherein the structural information is indicative of:
a height, shape, number, and/or distribution of pilling on the textile; and/or
a type of fasteners on the textile.

2. Method according to claim 1, wherein the structural information is indicative of the height, the shape and/or the number of pilling on the textile.

3. Method according to claim 1, wherein the at least one treatment parameter is indicative of a recommendation of pretreatment, a cleaning treatment and/or a final treatment of the textile, and/or
wherein the at least one treatment parameter is indicative of a cleaning agent type, a cleaning agent amount, a cleaning temperature, a cleaning device type, settings of a cleaning device, or a combination thereof.

4. Method according to claim 1, the method further comprising:

carrying out a treatment of the textile or prompting said treatment to be carried out in accordance with the at least one ascertained treatment parameter by employing at least one treatment device.

5. Method according to claim 1, wherein the structural information is determined before, during and/or after a treatment of the textile.

6. Method according to claim 1, wherein determining the structural information of the textile is conducted with at least one optical sensor element.

7. Method according to claim 6, wherein the optical sensor element provides a three-dimensional spatial resolution.

8. Method according to claim 6, wherein the at least one optical sensor element comprises at least one camera-like element and provides image information about the textile.

9. Method according to claim 8, wherein the image information comprises at least two individual images of the textile.

10. Method according to claim 1, wherein the structural information of the textile further comprises image information of lettering of a marking of the textile.

11. Method according to claim 1, wherein determining the structural information of the textile is conducted with at least one acoustic sensor element.

12. Method according to claim 1, the method further comprising:
exposing the textile to a stimulus.

13. Method according to claim 1, the method further comprising:
determining a user profile at least in part on the basis of the structural information,
wherein the ascertainment of the at least one treatment parameter takes place at least in part on the basis of the user profile.

14. Device that is configured for or that comprises corresponding features for carrying out and/or controlling a method according to claim 1.

15. System, comprising:
at least one mobile appliance and a treatment device which together carry out a method according to claim 1.

16. Method according to claim 1, wherein nondestructively determining structural information comprises nondestructively determining image information about the textile using at least one optical sensor element comprising at least one camera-like element, wherein the image information comprises at least two individual images of the textile and wherein image information is of lettering of a marking of the textile.

17. Method according to claim 16, wherein determining the image information includes carrying out character recognition and/or classification of the lettering.

18. Method according to claim 16, further comprising exposing the textile to a stimulus comprising radiation.

19. Method according to claim 1, further comprising exposing the textile to a stimulus comprising a sound, and wherein nondestructively determining structural information comprises nondestructively determining acoustic information about the textile using at least one acoustic sensor element.

20. Method according to claim 1, wherein the structural information is indicative of the type of fasteners on the textile.

* * * * *